United States Patent [19]
Lee

[11] Patent Number: 5,806,540
[45] Date of Patent: Sep. 15, 1998

[54] TOOTH PICK WITH FLEXIBLE HOLLOW BODY

[76] Inventor: Wan K. Lee, 11722 Westshore Ct., Cupertino, Calif. 95014

[21] Appl. No.: 745,229

[22] Filed: Nov. 18, 1996

[51] Int. Cl.⁶ .................................................. A61C 15/02
[52] U.S. Cl. ............................................................. 132/329
[58] Field of Search .................................... 132/321, 323, 132/329, 328; 433/142, 141, 166, 216, 119

[56] References Cited

U.S. PATENT DOCUMENTS

| | | | |
|---|---|---|---|
| D. 309,040 | 7/1990 | Poon . | |
| 431,713 | 7/1890 | Whaley | 132/329 |
| 710,498 | 10/1902 | McClain . | |
| 774,253 | 11/1904 | Keepe | 433/142 |
| 1,058,234 | 4/1913 | Hamilton | 132/321 |
| 1,989,895 | 2/1935 | Gilder . | |
| 2,562,587 | 7/1951 | Swearingern | 433/166 |
| 3,247,857 | 4/1966 | Kanbar . | |
| 3,511,249 | 5/1970 | Baitz . | |
| 4,805,646 | 2/1989 | Shimenkov . | |
| 4,852,728 | 8/1989 | Court . | |

FOREIGN PATENT DOCUMENTS

| | | | |
|---|---|---|---|
| 2 431 283 | 2/1980 | France . | |
| 2659846 | 9/1991 | France | 433/142 |
| 2209562 | 9/1973 | Germany | 433/166 |

*Primary Examiner*—Todd E. Manahan
*Assistant Examiner*—Eduardo C. Robert
*Attorney, Agent, or Firm*—Jacobson, Price, Holman & Stern, PLLC

[57] ABSTRACT

A tooth pick includes a hollow body, a rib provided in the middle of the hollow body, and a head part. The head part includes a tip which is an extension of the rib, an inclined section which is an extension of the hollow body, and a sealing wall formed between the hollow body and the tip. The sealing wall seals air in the hollow body.

17 Claims, 4 Drawing Sheets

FIG. 1.1

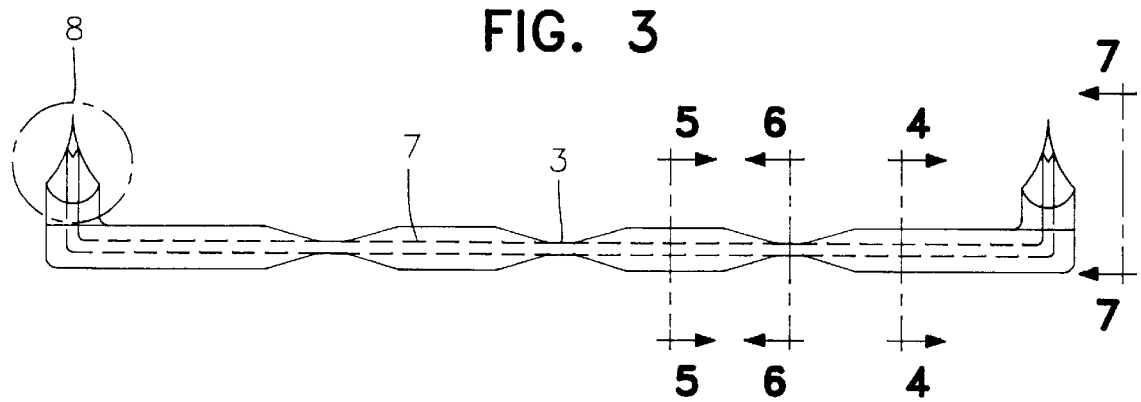
FIG. 3
FIG. 3.1
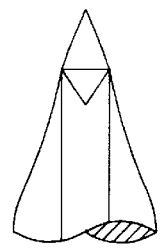
FIG. 4     FIG. 5     FIG. 6
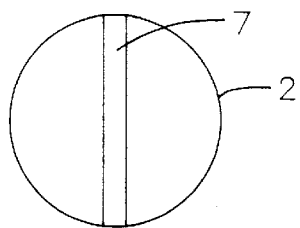 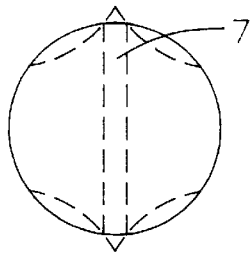 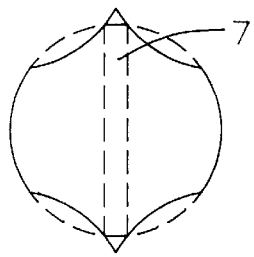
FIG. 7
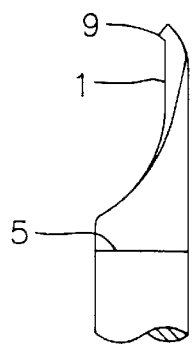

TOOTH PICK WITH FLEXIBLE HOLLOW BODY

BACKGROUND OF THE INVENTION

1. Field of the Invention

The present invention relates to a tooth pick. More particularly, the present invention relates to a tooth pick with a hollow body that has a pointed tip of a rib attached to a flexible hollow body.

2. Description of Related Art

The Mclain patent, U.S. Pat. No. 710,498, discloses a tooth pick in combination with the quill or pick proper of a point-retaining device provided with a right-angular passage or seat adapted to be slipped bodily over the entire end of the pick. The point of the pick will extend through the angular passage or seat and be held at a substantially right angle to the body of the quill.

The Shimenkov patent, U.S. Pat. No. 4,805,646, discloses a tooth pick which has a body part with two body portions that are movable relative to one another to assume different angles. The tooth pick can be filled with a substance which may be expelled by squeezing or displacing a part of it. Both ends of the tooth pick can be formed as working ends with different sizes.

SUMMARY OF THE INVENTION

The present invention is directed to a tooth pick that substantially obviates one or more of the problems due to limitations and disadvantages of the related art.

A primary object of the present invention is to provide a tooth pick with a flexible hollow body to be inserted into an embrassure or opening between adjacent teeth.

Another object of the present invention is to provide a tooth pick with a pointed tip of a rib which has a diamond-shaped top and a triangular-shaped front that conforms to the embrassure and can effectively remove food residuals from between the teeth.

Another object of the present invention is to provide a tooth pick that can effectively remove plaque, tartar and germ built on the sides of teeth by lifting the tooth pick to reduce various dental diseases.

Another object of the present invention is to provide a tooth pick that can be manufactured inexpensively, but which is effectively in preserve the teeth in a healthy condition.

Another object of the present invention is to provide a tooth pick that is lightweight so that a user can carry it easily in the user's pocket and can use it anytime when the user desires.

Another object of the present invention is to provide a tooth pick with having a slanted bevel formed under the tip of the tooth pick to protect free gingiva from hurting while the tooth pick is being inserted into the embrassure.

Further objects of the invention will be clear as the description proceeds.

To achieve these objects and provide other advantages, and in accordance of the purpose of the invention as embodied and broadly described, the invention provides a tooth pick including a hollow body, a rib provided in the middle of the hollow body, a tip which is an extension of the rib, and a sealing wall formed between the hollow body and the tip. The sealing wall is for sealing air in the hollow body. The invention may be embodied in the form illustrated in the associated drawings. Attention is called to the fact, however, that the drawings are for illustrative purposes only, and that changes may be made in the specific construction illustrated and described within the scope of the appended claims.

BRIEF DESCRIPTION OF THE DRAWINGS

FIG. 1.1 is an enlarged portion of the tooth pick engaged with teeth.

FIG. 3 is a top view of the unfolded tooth pick according to the preferred embodiment of the present invention.

FIG. 3.1 is an enlarged top view of a head part of FIG. 3.

FIG. 4 is a cross-sectional view of the hollow body with a rib as seen in the direction of arrow 4 in FIG. 3.

FIG. 5 is a sectional view of the hollow body with a rib as seen in the direction of arrow 5 in FIG. 3.

FIG. 6 is a sectional view of the hollow body with a rib as seen in the direction of arrow 6 in FIG. 3.

FIG. 7 is a side view of the head part according to the present invention as seen in the direction of arrow 7 in FIG. 3.

DETAILED DESCRIPTION OF THE PREFERRED EMBODIMENTS

Reference will now be made in detail to the preferred embodiments of the invention, an example of which is illustrated in the accompanying drawings.

Figure 1:
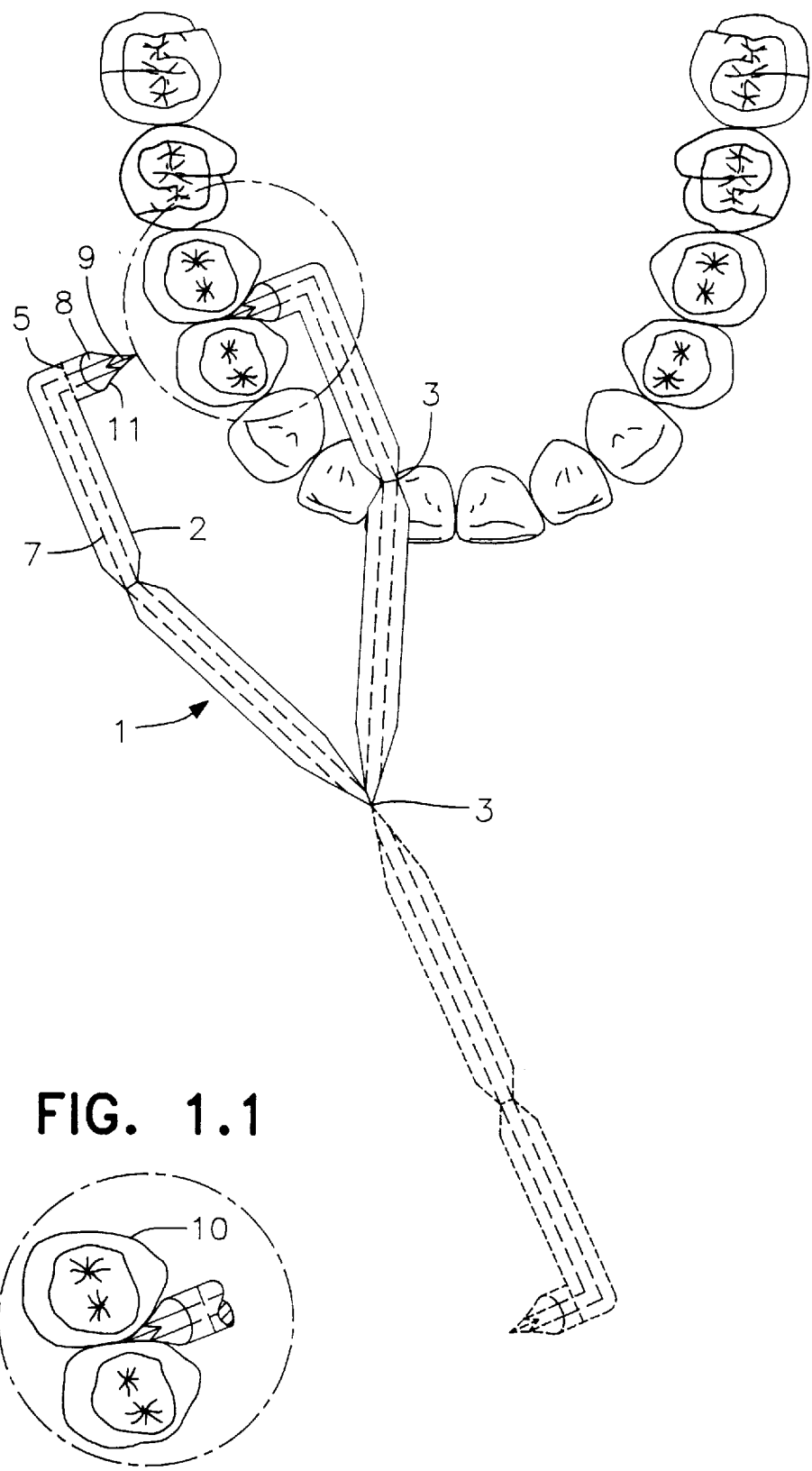
FIG. 1 is a top view of the tooth pick engaged with teeth according to a preferred embodiment of the present invention.

FIG. 1 illustrates a preferred embodiment of the present invention. As shown in FIG. 1, a flexible tooth pick according to the present invention is designated generally by reference numeral 1 and includes a hollow body 2, a head part 8, hinges 3 formed by crimping and separate ribs 7. Each rib 7 is located so that it extends diametrically over a cross section of the hollow body 2. The head part 8 includes a sealing wall 5, a pointed tip 9 of the rib 7 which is formed by an extension of one of the ribs 7, and an inclined section 11 of the hollow body 2. FIG. 1 includes an enlarged portion showing how the tooth pick 1 engages with the teeth 10.

The head part 8, according to the preferred embodiment, is formed perpendicular to the immediately adjacent connected portion of the hollow body 2 so as to be easily inserted into an embrassure (not shown) without hurting a free gingiva 13.

The pointed tip 9 of the rib 7 is inserted into an embrassure using flexible movement of the hollow body 2. As shown in FIG. 1, two pointed tips 9 of opposed ribs 7 can be inserted into the embrassure at the same time to effectively remove food residuals, plaque and tartar. Each pointed tip 9 of a rib 7 has a diamond-shaped top and a triangular-shaped front to conform to a triangular-shaped embrassure. The sealing wall 5 is provided to seal the air in the hollow body 2 to preserve the flexibility of the hollow body 2. Ribs 7 are provided in the middle of hollow body 2 to provide a minimum strength to the hollow body 2 and to reinforce the tooth pick 1. The hollow body 2 can be made of aluminum, plastic or tungsten that is lightweight. Since the hollow body 2 includes air, and flexible ribs 7 are formed inside the hollow body 2, the tooth pick 1 can be flexible and adaptable to any type or shape of teeth.

The inclined section 11 of the hollow body 2 is provided to remove the tartar or plaque which has built up on the side body of the teeth 10. The tartar or plaque which has built up on the side body of the teeth 10 is usually hard to remove by using a brush, dental floss or an ordinary tooth pick. According to the present invention, after a pointed tip 9 of a rib 7 is inserted into the embrassure until the inclined section 11 contacts with the side body of the teeth 10, the tooth pick 1 can be lifted and lowered repeatedly while maintaining the contact with the teeth 10. During this action, the tooth pick 1 can effectively remove tartar, plaque and germs which have built up on the sides of the teeth 10.

Since each pair of head parts 8 is perpendicular to the immediately connected hollow body 2 according to the preferred embodiment of the present invention, the tooth pick 1 can also remove tartar, plaque and germs which have built up on the interior sides of the teeth 10.

Figure 2:
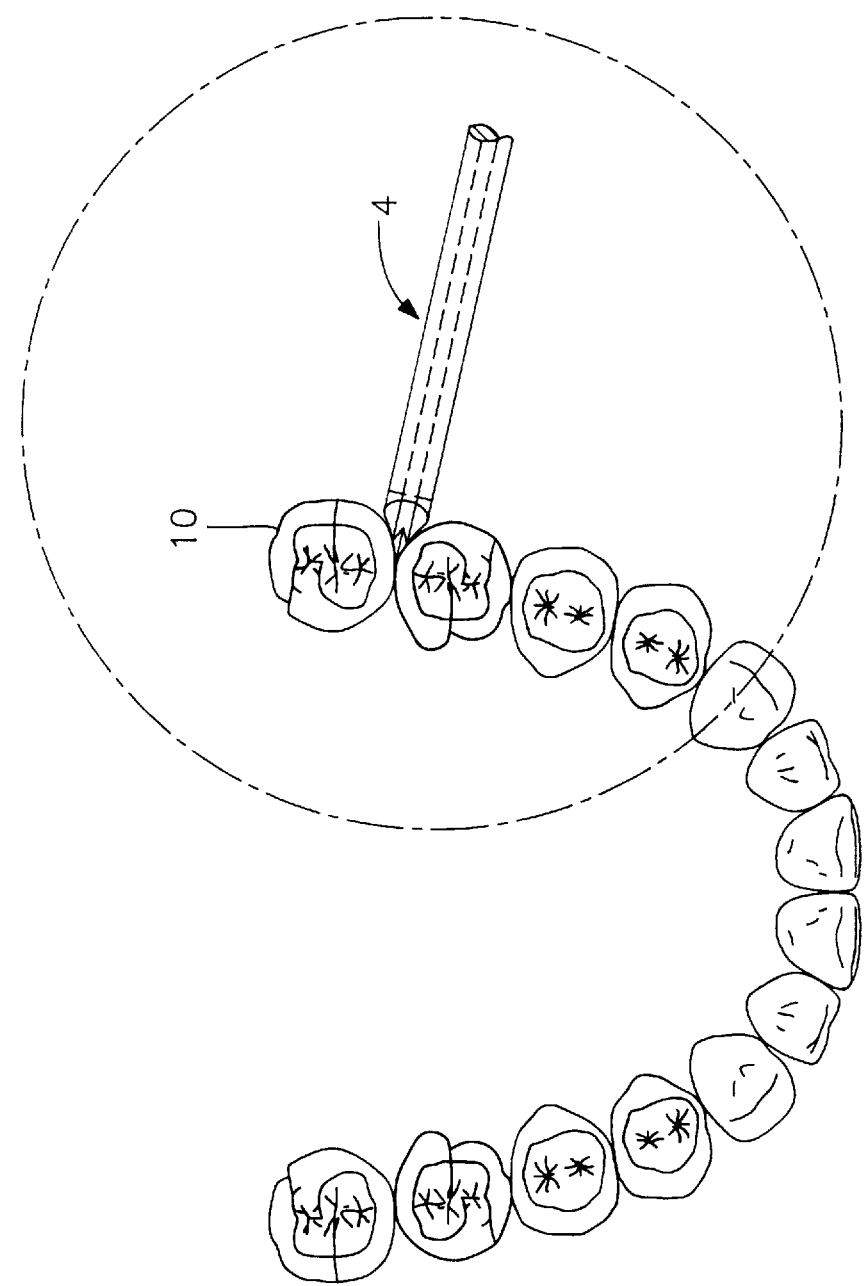
FIG. 2 is a top view of the tooth pick engaged with teeth according to a second embodiment of the present invention.

FIG. 2 illustrates a single tooth pick according to a second embodiment of the present invention. The tooth pick 4 has generally the same structure as the tooth pick 1 as shown in FIG. 1. According to the second embodiment of the present invention, the head part 8 is an extension of the hollow body 2. The tooth pick 4 according to the second embodiment of the present invention can be used in the same way as other typical tooth picks; the pointed tip 9 of the rib 7 of the tooth pick 4 can be inserted into an embrassure from only one direction.

FIG. 3 illustrates the unfolded tooth pick 1 according to the preferred embodiment of the present invention. An enlarged top view of a head part 8 also forms part of the illustration provided by FIG. 3.

FIGS. 4–6 illustrate cross-sectional views of the hollow body 2 with a rib 7, according to the preferred embodiment of the present invention, as seen in the directions of arrows 4, 5 and 6 in FIG. 3, respectively.

FIG. 7 is a side view of the head part 8. As shown in FIG. 7, the pointed tip 9 of a rib 7 has a diamond-shaped top and a triangular-shaped front (better seen in FIG. 11). The line indicates the sealing wall 5 which seals the air in the hollow body 2 to preserve the flexibility of the hollow body 2 and prevents debris from entering the interior of the hollow body 2.

Figure 10:
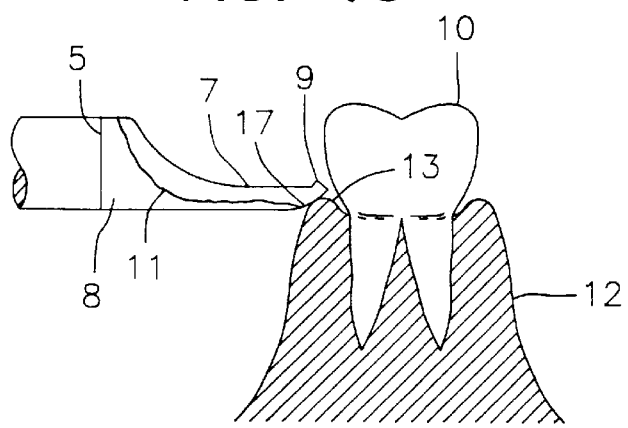
FIG. 10 is a side view of the head part with a tooth surrounded by gingiva according to the present invention.

Under the pointed tip 9 of the rib 7, the rib 7 is cut to form a round-shaped slanted bevel 17 for protecting free gingiva 13. The bevel 17 is better seen in FIG. 10. The round shape of the bevel prevents the bevel from hurting a user when the tooth pick 1 is inserted into the embrassure. The term "free gingiva" 13 is used to designate an extension of a gingiva 12 that is not fixed to the roots of the teeth 10. Since the free gingiva 13 is flexible and is not fixed to the teeth 10, it is easy for the free gingiva to be pricked by the ordinary tooth picks. However, the round-shaped slanted bevel 17 formed at the head part 8 according to the present invention provides a soft contact with the free gingiva 13 when the tooth pick 1 is being inserted into the embrassure. Preferably, the slope of the slanted bevel is about 45 degrees relative to horizontal, as shown in FIG. 10, so that the tooth pick 1 can be slipped over the free gingiva and between the free gingiva and the enamel of the tooth without pricking the free gingiva.

The pointed tip 9 of the rib 7 conforms well to an embrassure so that the flexible contact with the embrassure is improved. The device can be used in this way for effectively cleaning the teeth. By using this tooth pick according to the present invention, food residuals, plaque and tartar built up on the side body of the teeth 10, which ordinarily cannot be removed by brushing or using dental floss, can be removed effectively.

Figure 8:
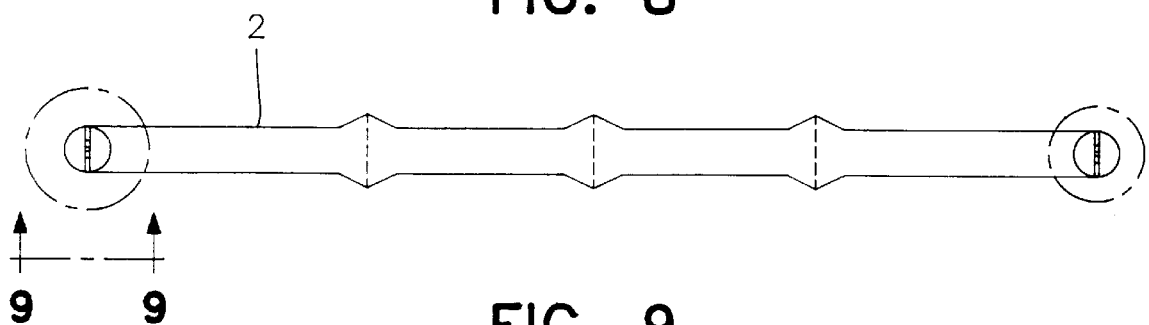
FIG. 8 is a front view of the tooth pick according to the preferred embodiment of the present invention.

FIG. 8 shows a front view of the tooth pick 1 according to the preferred embodiment of the present invention.

Figure 9:
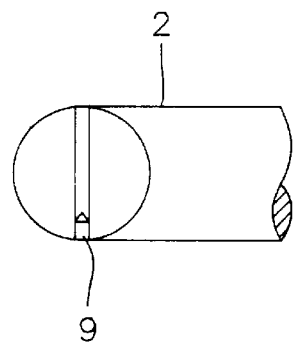
FIG. 9 is a front view of the head part according to the preferred embodiment of the present invention as seen in the direction of arrow 9 in FIG. 8.

FIG. 9 shows a front view of the head part 8 of the tooth pick 1 according to the preferred embodiment of the present invention. FIG. 9 also illustrates a triangular-shaped front of the tip 9.

FIG. 10 better illustrates how the slanted bevel 17 is utilized to protect the free gingiva 13 from being pricked when the tooth pick 1 is being inserted into the embrassure.

Figure 11:
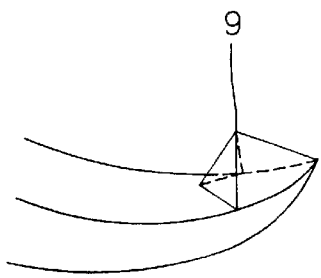
FIG. 11 is a three-dimensional view of the tip according to the present invention.

FIG. 11 better illustrates the pointed tip 9 of the rib 7 in three dimensions. As shown in FIG. 11, the front shape of the tip 9 is triangular and, thus, the tip 9 conforms to the triangular-shaped embrassure. FIG. 11 further illustrates the slanted bevel 17 which facilitates the insertion of the tip 9 without hurting the free gingiva 13.

It will be apparent to those skilled in the art that various modifications can be made in the tooth pick without departing from the spirit or scope of the invention. Thus, it is intended to cover modifications and variations of this invention within the scope of the appended claims and their equivalents.

What I claim is:

1. A tooth pick, comprising:

a hollow body;

a flexible rib provided in middle of said hollow body; and a tip attached perpendicular to said hollow body, wherein said tip is an extension of said rib.

2. A tooth pick according to claim 1, wherein said tip has a triangular-shaped front.

3. A tooth pick according to claim 1, further comprising an inclined section which is an extension of said hollow body.

4. A tooth pick according to claim 1, wherein said hollow body is made of a material selected from the group consisting of tungsten, plastic and aluminum.

5. A tooth pick according to claim 1, further comprising a slanted bevel formed under said tip.

6. A tooth pick comprising:

a hollow body;

a flexible rib provided in middle of said hollow body; and a tip defined by an extension of said rib and attached perpendicular to said hollow body.

7. A tooth pick according to claim 6, further comprising a slanted bevel formed under said tip.

8. A tooth pick according to claim 6, wherein said tip has a diamond-shaped top and a triangular-shaped front.

9. A tooth pick according to claim 6, wherein said hollow body is made of a material selected from the group consisting of tungsten, plastic and aluminum.

10. A tooth pick comprising:

a hollow body;

a flexible rib provided in middle of said hollow body; and a head part comprising:

a tip attached perpendicular to said hollow body, wherein said tip is an extension of said rib; and an inclined section which is an extension of said hollow body.

11. A tooth pick according to claim 10, further comprising a slanted bevel formed under said tip.

12. A tooth pick according to claim 10, wherein said hollow body is made of a material selected from the group consisting of tungsten, plastic and aluminum.

13. A tooth pick according to claim 10, wherein said tip has a diamond-shaped top and a triangular-shaped front.

14. A tooth pick comprising a pair of tips;

a hollow body; and a flexible rib provided in middle of the hollow body, wherein the tips are extensions of said rib at both ends of said rib and are attached perpendicular to said hollow body;

wherein said pair of tips can be inserted into an inner and an outer side of an embrasure at the same time.

15. A tooth pick according to claim 14, further comprising a slanted bevel formed under each of said tips.

16. A tooth pick according to claim 14, wherein each of said tips has a diamond-shaped top and a triangular-shaped front.

17. A tooth pick according to claim 14, wherein said hollow body is made of a material selected from the group consisting of tungsten, plastic and aluminum.

* * * * *